(12) United States Patent
Andrews et al.

(10) Patent No.: US 12,123,304 B2
(45) Date of Patent: Oct. 22, 2024

(54) SYSTEMS AND METHODS FOR MONITORING GAS STORAGE IN UNDERGROUND RESERVOIRS

(71) Applicant: Schlumberger Technology Corporation, Sugar Land, TX (US)

(72) Inventors: Albert Ballard Andrews, Wilton, CT (US); Andrew J. Speck, Milton, MA (US); Ridvan Akkurt, Denver, CO (US); Oliver C. Mullins, Houston, TX (US); Shawn David Taylor, Reading, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 18/559,190

(22) PCT Filed: May 6, 2022

(86) PCT No.: PCT/US2022/028064
§ 371 (c)(1),
(2) Date: Nov. 6, 2023

(87) PCT Pub. No.: WO2022/236048
PCT Pub. Date: Nov. 10, 2022

(65) Prior Publication Data
US 2024/0240558 A1 Jul. 18, 2024

Related U.S. Application Data

(60) Provisional application No. 63/201,666, filed on May 7, 2021.

(51) Int. Cl.
*G01J 3/44* (2006.01)
*E21B 47/113* (2012.01)
(Continued)

(52) U.S. Cl.
CPC ........ *E21B 49/0875* (2020.05); *E21B 47/114* (2020.05); *G01N 21/65* (2013.01); *G01N 33/2835* (2013.01); *B65G 5/00* (2013.01)

(58) Field of Classification Search
CPC ... E21B 49/0875; E21B 47/114; G01N 21/65; G01N 33/2835; G01N 21/783; G01J 3/44; G01J 3/02; G01J 3/28; B65G 5/00
See application file for complete search history.

(56) References Cited

U.S. PATENT DOCUMENTS 8,939,021 B2 * 1/2015 Daniel .................... E21B 49/10
73/152.04
9,359,883 B2 6/2016 Whittaker
(Continued)

FOREIGN PATENT DOCUMENTS

WO 2014172365 A1 10/2014

OTHER PUBLICATIONS

International search report and written opinion issued in the PCT Application PCT/US2022/028064, dated Aug. 31, 2022 (8 pages).
(Continued)

*Primary Examiner* — Abdullahi Nur
(74) *Attorney, Agent, or Firm* — Ashley E. Brown

(57) ABSTRACT

Systems and methods presented herein are configured to monitor gas storage in a well and, more specifically, to invert optical measurements to predict the fractional molar composition of an unknown composition of a gas mixture comprised of hydrogen, carbon dioxide, other gases, or combinations thereof, in any underground reservoir or salt dome where hydrogen, carbon dioxide, and/or the other gases are stored or exist.

20 Claims, 6 Drawing Sheets

(51) Int. Cl.
*E21B 49/08* (2006.01)
*G01N 21/65* (2006.01)
*G01N 33/28* (2006.01)
*B65G 5/00* (2006.01)

(56) References Cited

U.S. PATENT DOCUMENTS

| | | | |
|---|---|---|---|
| 10,012,758 | B2 | 7/2018 | Speck |
| 10,088,422 | B2 | 10/2018 | Andrews |
| 10,767,475 | B2* | 9/2020 | Stone ................ E21B 43/00 |
| 2007/0119244 | A1 | 5/2007 | Goodwin et al. |
| 2008/0141767 | A1* | 6/2008 | Raghuraman ...... G01N 33/2823 |
| | | | 73/152.55 |
| 2009/0125238 | A1* | 5/2009 | Barboza ............. E21B 49/0875 |
| | | | 702/11 |
| 2012/0203525 | A1* | 8/2012 | Rodriguez Herrera ...................... |
| | | | E21B 47/022 |
| | | | 703/2 |
| 2013/0071934 | A1 | 3/2013 | Indo |
| 2014/0260586 | A1* | 9/2014 | Van Hal ................ E21B 49/082 |
| | | | 73/152.11 |
| 2016/0177716 | A1 | 6/2016 | Zuo |
| 2020/0240264 | A1 | 7/2020 | He |

OTHER PUBLICATIONS

International Preliminary Report on Patentability issued in the PCT Application PCT/US2022/028064 dated Nov. 16, 2023, 5 pages.

\* cited by examiner

SYSTEMS AND METHODS FOR MONITORING GAS STORAGE IN UNDERGROUND RESERVOIRS

CROSS-REFERENCE TO RELATED APPLICATION

This application claims priority to and the benefit of U.S. Provisional Patent Application Ser. No. 63/201,666, entitled "Method and Apparatus for Monitoring Gas Storage in Underground Reservoirs," filed May 7, 2021, which is hereby incorporated by reference in its entirety for all purposes.

FIELD OF INVENTION

The present disclosure generally relates to systems and methods for monitoring gas storage in a well and, more specifically, to inverting optical measurements to predict the fractional molar composition of an unknown composition of a gas mixture comprised of hydrogen, carbon dioxide, other gases, or combinations thereof, in any underground reservoir or salt dome where hydrogen, carbon dioxide, and/or the other gases are stored or exist.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Existing downhole logging tools use visible and near-infrared (Vis/NIR) absorption to measure composition of reservoir fluids and water. Methane ($CH_4$), Carbon dioxide ($CO_2$), and hydrogen sulfide ($H_2S$), and other polyatomic molecules, are infrared and Raman active. In contrast, diatomic molecules such as hydrogen ($H_2$) and nitrogen ($N_2$) are only Raman active, and $H_2S$ absorption bands in the Vis/NIR portion of the electromagnetic spectrum are relatively weak. In addition, $CO_2$ absorption bands in the Vis/NIR portion of the electromagnetic spectrum may be obscured by the presence of water. The Raman bands of water do not interfere with gases in the mid-long wavelength infrared region (e.g., 3-15 microns) and are weak in the fingerprint region where fundamental vibrations probed by Raman are located. There are currently no logging tools that can measure the key gases pertinent to hydrogen (or other gas) storage and, thus, that can detect changes in composition due to chemical, microbial or migration processes in a depleted reservoir utilized for hydrogen (or other gas) storage. Therefore, a downhole logging tool suitable for monitoring hydrogen (or other gas) storage wells and carbon capture storage wells may exploit Raman spectroscopy.

The Raman peak intensity is proportional to the molar density of a chemical moiety. Raman scattered photons may be detected in a back-scattering geometry, which is advantageous for a slim tool production logging tool. However, the biggest challenge to performing Raman spectroscopy in a wellbore is the laser requirement: a high intensity narrow band laser as described in U.S. Pat. No. 10,012,758 and a high temperature Raman spectrometer as described in U.S. Pat. No. 10,088,422. In addition, commingled flow requires knowledge of the flow rates for contributing zones, as described in U.S. Pat. No. 9,359,883.

SUMMARY

A summary of certain embodiments described herein is set forth below. It should be understood that these aspects are presented merely to provide the reader with a brief summary of these certain embodiments and that these aspects are not intended to limit the scope of this disclosure.

Certain embodiments of the present disclosure include a data processing system that includes one or more processors configured to execute instructions stored on one or more memory media. The instructions, when executed by the one or more processors, cause the data processing system to monitor storage of gas in a well by: estimating initial mole fractions of one or more components of the gas being stored in the well based on one or more tool parameters of a logging tool disposed within a wellbore of the well in a zone of a subterranean formation; calculating component densities of the one or more components of the gas based at least in part on the initial mole fractions of the one or more components of the gas; predicting an optical response and pressure using the one or more tool parameters of the logging tool and the component densities of the one or more components of the gas; and comparing the predicted optical response and pressure to an optical response and pressure measured by an optical module of the logging tool to determine whether the estimated initial mole fractions and the calculated component densities of the one or more components of the gas are representative of actual mole fractions and component densities of the one or more components of the gas.

Certain embodiments of the present disclosure also include a method for monitoring storage of gas in a well that includes estimating, via a data processing system, initial mole fractions of one or more components of the gas being stored in the well based on one or more tool parameters of a logging tool disposed within a wellbore of the well in a zone of a subterranean formation. The method also includes calculating, via the data processing system, component densities of the one or more components of the gas based at least in part on the initial mole fractions of the one or more components of the gas. The method further includes predicting, via the data processing system, an optical response and pressure using the one or more tool parameters of the logging tool and the component densities of the one or more components of the gas. In addition, the method includes comparing, via the data processing system, the predicted optical response and pressure to an optical response and pressure measured by an optical module of the logging tool to determine whether the estimated initial mole fractions and the calculated component densities of the one or more components of the gas are representative of actual mole fractions and component densities of the one or more components of the gas.

Certain embodiments of the present disclosure also include a logging tool includes an optical module and a data processing system configured to monitor storage of gas in a well. The data processing system is configured to estimate initial mole fractions of one or more components of gas being stored in a well based on one or more tool parameters of the logging tool. The data processing system is also configured to calculate component densities of the one or more components of the gas based at least in part on the initial mole fractions of the one or more components of the gas. The data processing system is further configured to predict an optical response and pressure using the one or more tool parameters of the logging tool and the component densities of the one or more components of the gas. In addition, the data processing system is configured to compare the predicted optical response and pressure to an optical response and pressure measured by the optical module to determine whether the estimated initial mole fractions and the calculated component densities of the one or more components of the gas are representative of actual mole fractions and component densities of the one or more components of the gas.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings, in which.

DETAILED DESCRIPTION

Figure 1:
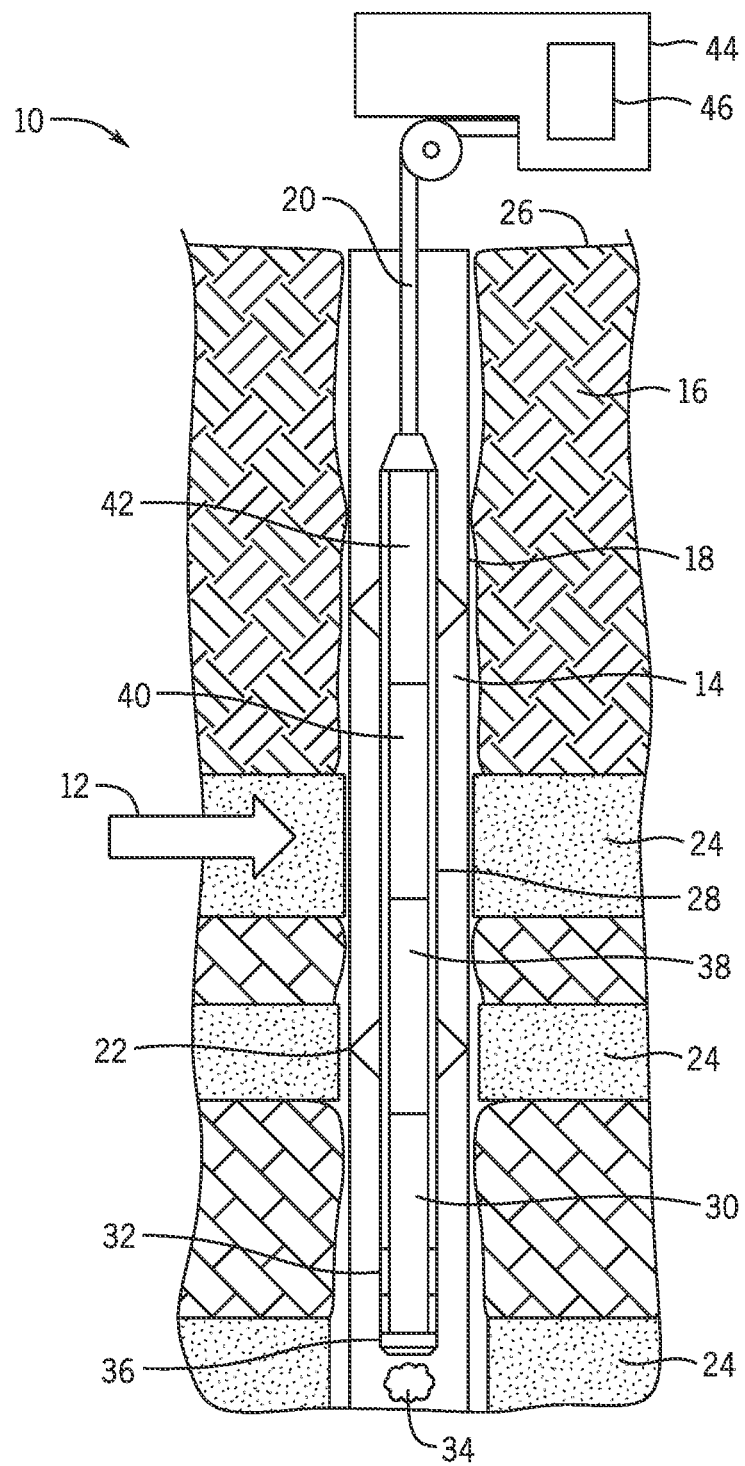
FIG. 1 is a schematic diagram of a system for monitoring gas storage (e.g., including hydrogen, carbon dioxide, and/or other gases) in underground reservoirs, in accordance with embodiments of the present disclosure.

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

As used herein, the terms "connect," "connection," "connected," "in connection with," and "connecting" are used to mean "in direct connection with" or "in connection with via one or more elements"; and the term "set" is used to mean "one element" or "more than one element." Further, the terms "couple," "coupling," "coupled," "coupled together," and "coupled with" are used to mean "directly coupled together" or "coupled together via one or more elements."

In addition, as used herein, the terms "real time", "real-time", or "substantially real time" may be used interchangeably and are intended to describe operations (e.g., computing operations) that are performed without any human-perceivable interruption between operations. For example, as used herein, data relating to the systems described herein may be collected, transmitted, and/or used in control computations in "substantially real time" such that data readings, data transfers, and/or data processing steps occur once every second, once every 0.1 second, once every 0.01 second, or even more frequently, during operations of the systems (e.g., while the systems are operating). In addition, as used herein, the terms "continuous", "continuously", or "continually" are intended to describe operations that are performed without any significant interruption. For example, as used herein, control commands may be transmitted to certain equipment every five minutes, every minute, every 30 seconds, every 15 seconds, every 10 seconds, every 5 seconds, or even more often, such that operating parameters of the equipment may be adjusted without any significant interruption to the closed-loop control of the equipment.

In addition, as used herein, the terms "automatic", "automated", "autonomous", and so forth, are intended to describe operations that are performed are caused to be performed, for example, by a computing system (i.e., solely by the computing system, without human intervention). Indeed, it will be appreciated that the data processing systems described herein may be configured to perform any and all of the data processing and control functions described herein automatically.

Certain embodiments described herein include systems and methods for inverting optical measurements to predict the fractional molar composition of an unknown composition of a gas mixture comprised of hydrogen and other gases in any underground reservoir or salt dome where hydrogen and/or the other gases are stored or exists.

In certain embodiments, a model of the measurement response parameterized in terms of absolute number density of the components (e.g., mole/volume) may be inverted in combination with the prediction from an equation of state (EOS) describing number density as a function of mole fractions, pressure, and temperature of the gas. By matching the prediction from the forward model plus the EOS to the measured parameters, the absolute density measurements from the optical response may be converted to mole fractions.

In certain embodiments, the pressure and temperature information provide an additional degree of freedom to the fit. This allows either an absolute calibration factor or a plus fraction of components not resolved by the optical measurements to be inferred accurately. Tin certain embodiments, a Raman spectrograph may be used to detect vibrational and rotational modes of HH, CO, CH, HS, NN, NH, and SO between 400-4000 $cm^{-1}$ including, but not limited to hydrogen, carbon dioxide, carbon monoxide, methane, ethane, propane, nitrogen, ammonia, hydrogen sulfide, and/or other gases, as well as $H_2O$ (gas and or liquid phase).

FIG. 1 is a schematic diagram of a system 10 for monitoring gas storage (e.g., including hydrogen, carbon dioxide, and/or other gases, as described herein) in underground reservoirs. The system 10 illustrated in FIG. 1 includes a production gas composition logging tool 12 that is operable for conveyance within a wellbore 14 that traverses a subterranean formation 16. The wellbore 14 may include a casing 18 through which the logging tool 12 is conveyed via a wireline, slickline, and/or other cable 20. In certain embodiments, the logging tool 12 may include one or more centralizers 22 operable to aid in centering and/or otherwise orienting the logging tool 12 within the casing 18 and/or the wellbore 14. During production logging, formation fluid (e.g., formation liquid and/or formation gas) may be extracted from different zones, pay zones, and/or layers (hereafter collectively referred to simply as "zones") 24 of the formation 16. The logging tool 12 is operable to measure, detect, and/or monitor flow rate, composition, and/or other properties and characteristics of the formation fluid as the formation fluid flows to the surface 26.

The logging tool 12 includes a housing 28 that may contain or be at least partially formed by one or more modules. For example, one such module may be an optical module 30 operable to perform spectroscopic measurements on a sample of the formation fluid 34. In certain embodiments, the optical module 30 may be disposed at or near an end of the housing 28 (as shown in FIG. 1), and may be operable to perform Raman spectroscopy, laser induced breakdown spectroscopy, and/or other forms of spectrometry. The optical module 30 may include optics, a laser, and/or other light source, and one or more detectors. For example, in implementations in which the optical module 30 utilizes back-scattering spectroscopy, the laser and/or other light source may generate light that is utilized to analyze the formation fluid sample 34, where the light that scatters back from the sample 34 is detected by the one or more detectors. The optics of the optical module 30 are operable to, for example, communicate the light to and from the sample 34. For example, the optics of the optical module 30 may include a window 36 that may place the optical module 30 in optical communication with the formation fluid sample 34. As such, the formation fluid sample 34 adjacent the window 36 may be analyzed by the optical module 30. In the implementation illustrated in FIG. 1, the window 36 is located at a lower end of the logging tool 12. However, in other embodiments, instead of being located at the end of the logging tool 12, or in addition thereto, the window 36 may be located on a sidewall of the housing 28. In certain embodiments, the optics of the optical module 30 may include a high temperature Raman spectrograph 32. For example, in certain embodiments, the optics of the optical module 30 may include a Raman spectrograph 32 such as described in U.S. Pat. No. 10,088,422, which is hereby incorporated by reference in its entirety for all purposes. In certain embodiments, the Raman spectrograph 32 may use near infrared dielectric interference filters in lieu of a grating to detect the gas species of interest.

The logging tool 12 may also include one or more other modules that may operationally support the optical module 30. For example, in certain embodiments, the logging tool 12 may include a power module 38 operable to at least partially power the light source(s) and the detector(s) of the optical module 30. In addition, in certain embodiments, an amplification module 40 may be included in the logging tool 12 to, for example, amplify electrical and/or other signals output from the optical module 30. Such signals output from the optical module 30 may include one or more electrical and/or other type of signals that may be representative of light scattered back from the formation fluid sample 34 that is detected by the one or more detectors of the optical module 30. In addition, in certain embodiments, the logging tool 12 may also include a telemetry module 42 operable to provide communication between the logging tool 12 and surface equipment 44 (e.g., including a data processing system 46) located at the surface 26. For example, the telemetry module 42 may communicate electrical and/or other signals from the optical module 30 to the data processing system 46 located at the surface 26.

It should be noted that, in certain embodiments, a processing system of the logging tool 12 or another downhole tool may be used to perform the operations of the data processing system 46 described herein. In other words, as opposed to being located at the surface 26, the data processing system 46 described herein may be contained within the logging tool 12 or another downhole tool. In other embodiments, a processing system comprised of two processors, with one in the logging tool 12 or another downhole tool and one at the surface 26 may be configured to perform the operations described herein in conjunction with each other.

The logging tool 12 may be utilized in a comingled gas/gas condensate well according to the embodiments described herein. The pressures, temperatures, and fluid densities encountered in gas/gas condensate wells may produce a multi-phase flow with a phase separation as the gas and liquid flow to the surface 26. The phase separation may produce an annular flow pattern with the gas fraction flowing in the middle of the casing 18 and the fluid fraction flowing against the sides of the casing 18. In certain embodiments, the centralizers 22 may centrally position the optical sensor(s) to allow the gas fraction to be separately sampled, avoiding interference from the fluid fraction. The optical module 30 may be operable to analyze various different types of gases, including hydrogen ($H_2$), carbon dioxide ($CO_2$), carbon monoxide (CO), methane ($CH_4$), ethane ($C_2H_6$), propane ($C_3H_8$), butane ($C_4H_{10}$), pentane ($C_5H_{12}$), hexane ($C_6H_{14}$), heptane ($C_7H_{16}$), octane ($C_8H_{18}$), nonane ($C_9H_{20}$), decane ($C_{10}H_{22}$), hydrogen sulfide ($H_2S$), and nitrogen ($N_2$), among others. The optical module 30 may also be operable to analyze liquid fractions including hydrocarbons such as n-alkanes and/or other saturates, among other hydrocarbons, and/or aromatics such as benzene and m-xylene, among others. The liquid fraction may also include water and/or a multiphase mixture including one or more gases, liquid hydrocarbons, and/or water. The optical module 30 may also be operable to perform and/or otherwise utilize Raman spectroscopy in conjunction with a pulsed laser light source to determine the above examples of compositional components in the formation fluid sample 34, as described in greater detail herein.

One or more of the above-described modules 30, 38, 40, 42 and/or other modules of the logging tool 12 may also be operable to measure, sense, and/or detect pressure and/or temperature of fluid flow past the logging tool 12. In addition, in certain embodiments, one or more of the modules 30, 38, 40, 42 and/or other modules of the logging tool 12 may also include one or more controllers operable to at least partially control the functions described herein. In addition, in certain embodiments, one or more controllers of the modules 30, 38, 40, 42 may also be operable to communicate and/or work in conjunction with the data processing system 46.

Figure 2:
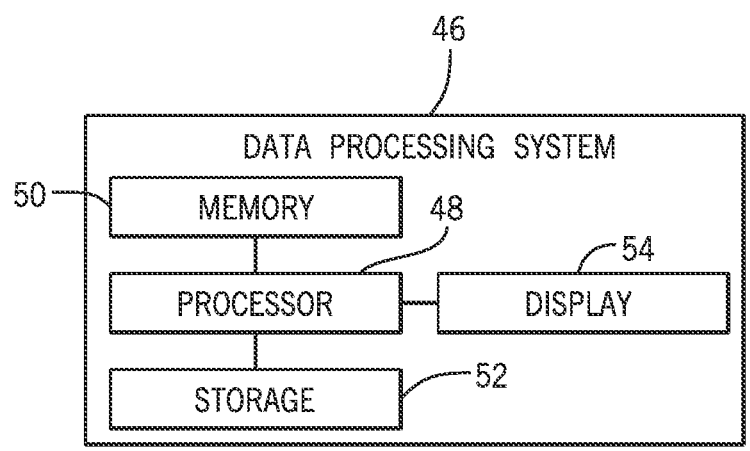
FIG. 2 is a schematic diagram of a data processing system of the system of FIG. 1, in accordance with embodiments of the present disclosure.

FIG. 2 is a schematic diagram of the data processing system 46 of FIG. 1. As described in greater detail herein, the logging tool 12 may obtain measurements relating to a formation fluid sample 34 for the purpose of monitoring gas storage (e.g., including hydrogen, carbon dioxide, and/or other gases, as described herein) in underground reservoirs. In certain embodiments, the data processing system 46 includes one or more processor(s) 48, memory media 50, storage media 52, and/or a display 54. In certain embodiments, the data processing system 46 may collect data from the logging tool 12 and determine one or more indices and indicators that, as described in greater detail herein, may enable monitoring of gas storage (e.g., including hydrogen, carbon dioxide, and/or other gases, as described herein) in underground reservoirs. Additionally or alternatively, the data processing system 46 may correlate a variety of data obtained throughout the creation of the well (e.g., design, drilling, logging, well completion, etc.) that may assist in the evaluation. Namely, the processor(s) 48, using instructions stored in the memory media 50 and/or storage media 52, may calculate the indicators and/or indices and/or may collect and correlate the other data into the evaluation. As such, the memory media 50 and/or the storage media 52 of the data processing system 46 may be any suitable article of manufacture that can store the instructions. The memory media 50 and/or the storage media 52 may be read-only memory (ROM), random-access memory (RAM), flash memory, an optical storage medium, or a hard disk drive, to name a few examples. The display 54 may be any suitable electronic display that can display logs, indices, and/or indicators that enable monitoring of gas storage (e.g., including hydrogen, carbon dioxide, and/or other gases, as described herein) in underground reservoirs, as described in greater detail herein.

Figure 3:
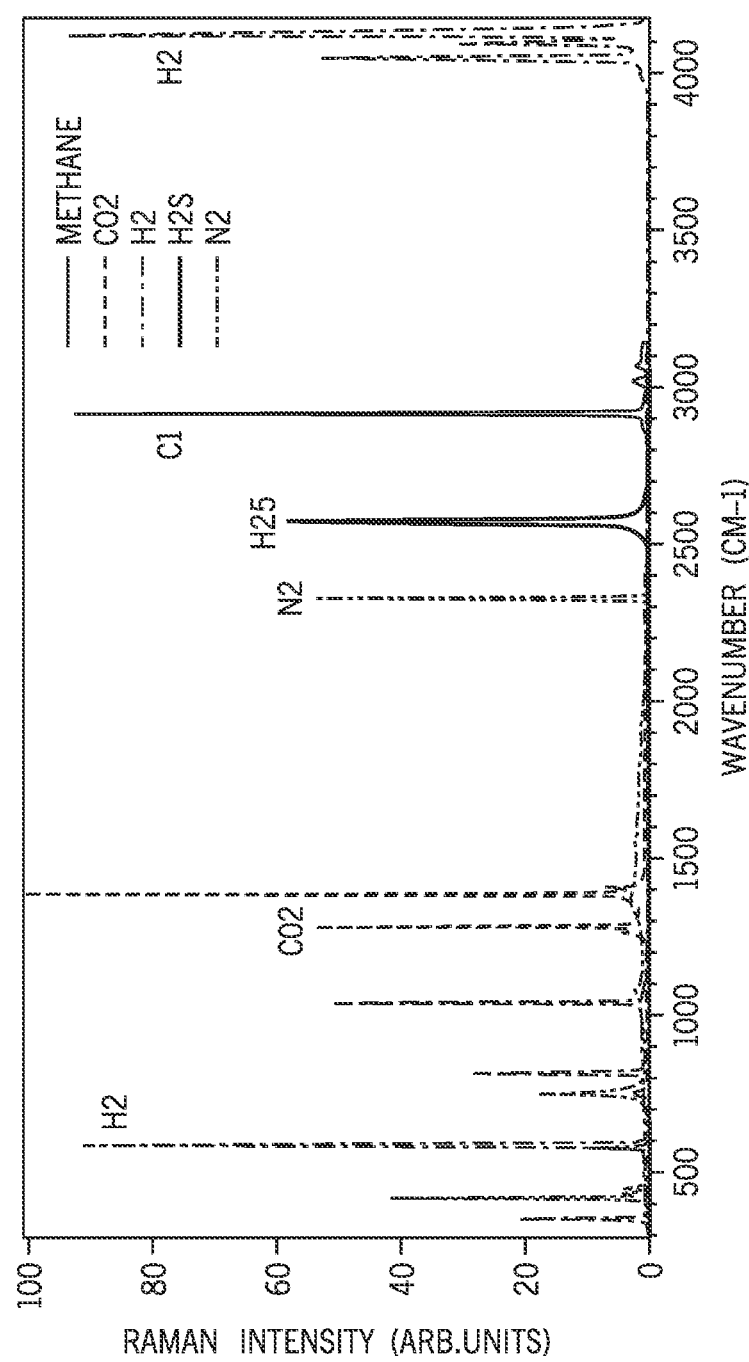
FIG. 3 illustrates a graph of Raman stretch modes of pure components for $H_2$, $N_2$, $CO_2$, $H_2S$ and $CH_4$, in accordance with embodiments of the present disclosure.

As described in greater detail herein, the logging tool 12, in combination with the data processing system 46, may be capable of determining fractional compositions of components of gas stored in underground reservoirs by analyzing data collected by the logging tool 12 described herein. For example, FIG. 3 illustrates a graph of Raman stretch modes of pure components for $H_2$, $N_2$, $CO_2$, $H_2S$, and $CH_4$ (illustrated in arbitrary units). As illustrated, $H_2$ has prominent rotational S branches around 584.5 $cm^{-1}$ and 1035 $cm^{-1}$ and a vibrational Q branch around 4046.5 $cm^{-1}$ and 4127 $cm^{-1}$. Methane has a CH stretch band around 2916 $cm^{-1}$ and $CO_2$ has two CO stretch bands around 1386 and 1281 $cm^{-1}$. In certain embodiments, the logging tool 12, in combination with the data processing system 46, may determine the mole fractions of hydrogen, carbon dioxide, methane, and hydrogen sulfide (as well as any of the other gases described herein), using data collected by the logging tool 12, which may have an internal gas reference cell containing a standard mixture of the target analytes in known concentrations. Such calculations may include correcting the measured hydrogen intensities by comparing the measured ratios of two or more HH vibrational and/or rotational bands with known ratios, in the event that unknown gases interfere with the hydrogen signal by cross absorption. In addition, the calculations may include inverting optical measurements to predict the fractional molar composition of the unknown composition of a gas mixture that allows either an absolute calibration factor or a plus fraction of components not resolved by the optical measurement to be inferred accurately.

In certain embodiments, the gases detected and analyzed may include, but are not limited to, hydrogen, methane, carbon dioxide, nitrogen, and hydrogen sulfide. The Raman spectrograph 32 detects the vibrational and rotational bands of $H_2$, $CO_2$, $CH_4$, $N_2$ and $H_2S$ functional groups spanning 400-4200 $cm^{-1}$. Hydrogen has prominent rotational S branches at 584.5 $cm^{-1}$ and 1035 $cm^{-1}$ and a vibrational Q branch around 4046.5 $cm^{-1}$ and 4127 $cm^{-1}$. Methane has a CH stretch band around 2916 $cm^{-1}$ and $CO_2$ has two stretch bands around 1386 and 1281 $cm^{-1}$. From the Raman intensities, the mole fractions of $H_2$, $CO_2$, $CH_4$, $N_2$ and $H_2S$ may be determined.

Figure 4:
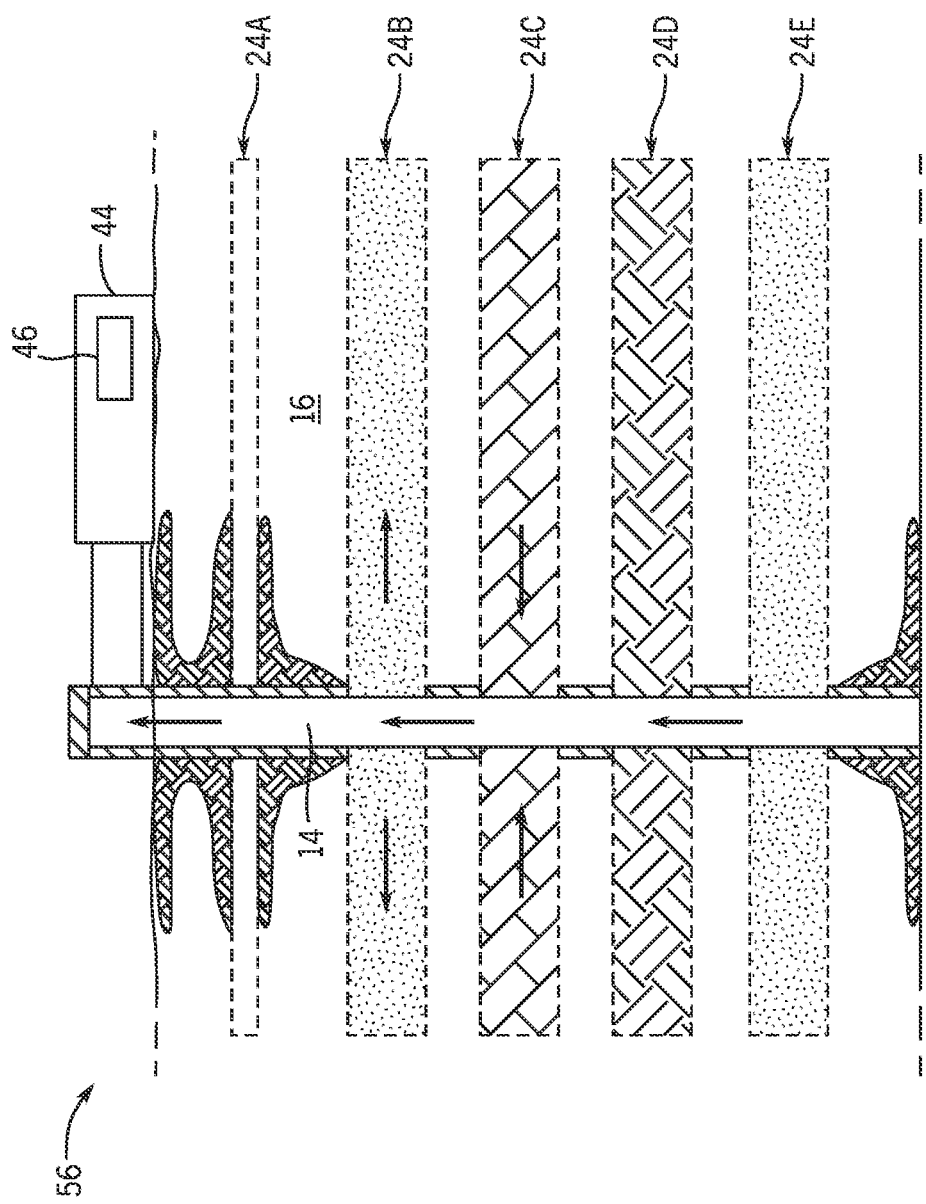
FIG. 4 illustrates a schematic of a hydrogen (or other gas) storage well that extends through a formation having various layers, in accordance with embodiments of the present disclosure.

FIG. 4 illustrates a schematic of a hydrogen (or other gas) storage well 56 that extends through a formation 16 having various layers 24 including, but not limited to, a cap rock layer 24A, a porous layer 24B, a microbial layer 24C, a salt layer 24D, and a cement layer 24E. Hydrogen may react with subsurface minerals in a depleted reservoir. The microbial layer 24C containing methanogens may consume either $CO_2$ or $H_2$ and produce $CH_4$ and/or $H_2S$ as an unwanted byproduct. The cement layer 24E may react with $H_2$. The porous layer 24B may lead to irrecoverable loss of hydrogen to the formation 16. Therefore, analysis using the logging tool 12 described herein may help with identifying gas content in the formation 16. If zones 24 are identified where microbial activity, chemical reactions, leakage, or other processes are occurring, these zones 24 may be shut in by the data processing system 46.

Figure 5:
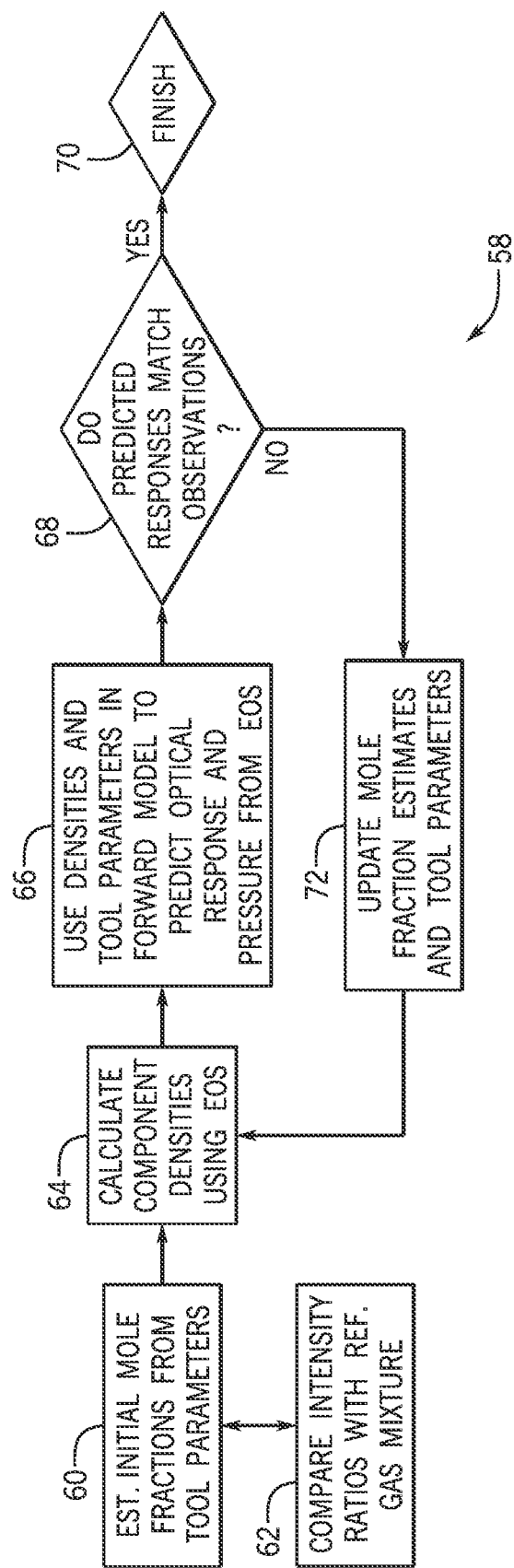
FIG. 5 is a flow diagram of a method that can be performed by the data processing system, which is in communication with a logging tool, to determine composition from molar densities of measured gases, in accordance with embodiments of the present disclosure.

FIG. 5 is a flow diagram of a method 58 that can be performed by the data processing system 46, which is in communication with the logging tool 12, to determine compositions from molar densities of measured gases, as described in greater detail herein. In operation, the logging tool 12 may be ran downhole and, at each zone (e.g., layer 24), tool parameters (e.g., such as temperature, pressure, fluid flow rates, measured refraction index, Raman spectrometer signals, and so forth) may be obtained by the logging tool 12. It will be appreciated that, in certain embodiments, the tool parameters may be obtained by downhole tools other than the logging tool 12. In certain embodiments, the data processing system 46, using the measurements at each zone, may estimate the initial mole fractions using the obtained parameters (block 60). In addition, in certain embodiments, the data processing system 46 may also compare the obtained Raman spectrometer signals with intensity ratios of one or more reference gases (block 62), for example, in an iterative manner. For example, pure gases may be measured in a laboratory, and a calibration file may be created that records the Raman intensity vs molar density. During a logging run, the calibration file may be used in conjunction with the inversion algorithms described herein to calculate the gas composition on a zone-by-zone basis in the wellbore 14. To first order, the Raman intensity is linearly proportional to the molar density. An additional linear response term $1+3r_m\rho_m$ (e.g., where the molar refractivity $r_m = 1/\rho_m \, (n^2-1)/(n^2+2)$, $\rho_m$ is the number density, and n is the index of refraction of the gas) may be included to account for index variations with gas density that effect the sample excitation volume, as described in U.S. Pat. No.

10,088,422. In certain embodiments, the data processing system 46 may then calculate component densities using a predefined EOS (block 64). In certain embodiments, the equation of state (EOS) may be one that accounts for interactions between molecules (e.g., a wide range natural gas EOS, the Refprop EOS, and so forth). In addition, in certain embodiments, the ideal gas law may also be used with a loss of accuracy, depending on which gases are present.

In addition, in certain embodiments, the data processing system 46 may use the calculated densities and the tool parameters of the logging tool 12 in a forward model to predict an optical response and pressure from the EOS (block 66). Then, in certain embodiments, the data processing system 46 may compare the predicted optical response and pressure to the measurements from the downhole tool (decision block 68). If the predicted optical response and pressure are both within respective predetermined thresholds of the measured optical response and pressure, the measurement is finished (block 70). This means that the estimated mole fractions and calculated component densities are correct, and the next zone 24 may be measured. Conversely, if the predicted optical response and pressure are not within respective predetermined thresholds of the measured optical response and pressure, the data processing system 46 may update the mole fraction estimate and the tool parameters of the logging tool 12 (block 72), and repeat steps 64, 66, and 68. In addition, in certain embodiments, the data processing system 46 may be configured to automatically adjust the tool parameters of the logging tool 12 based at least in part on the determination of the mole fractions and component densities. For example, in certain embodiments, the data processing system 46 may be configured to perform an intervention if certain unexpected results are detected by the data processing system 46. As but one non-limiting example, in certain situations, the data processing system 46 may be configured to adjust a concentration of hydrogen in a particular zone 24 if the data processing system 46 detects that the actual mole fractions and/or the actual component densities of hydrogen in the gas being analyzed in that particular zone 24 are outside of expected predetermined ranges for the mole fractions and/or component densities. Similar interventions may be performed for any of the other gas components described herein.

In certain embodiments, to determine the composition of each reservoir zone (e.g., layer) 24, the response of the logging tool 12 may be utilized by the data processing system 46 in conjunction with another production logging tool that can measure the total volumetric flow rate $Q_n$ above each layer 24 using standard production logging techniques. In such embodiments, the Raman spectrograph 32 of the logging tool 12 may return a signal proportional to the mass fractions of each component, measured at the same depths as $Q_n$. If the number of compositional components is y and $f_{n_x}$ is the mole fraction of the $x^{th}$ compositional component to the $n^{th}$ zone 24, it can be shown using the ideal gas law that the production fluid flow rates (of each component) are given by:

$$Q_{n_x} = \frac{f_{n_x}}{f_{n_1} + f_{n_2} + f_{n_3} + \ldots + f_{n_y}} Q_n \frac{P_n T_{ref} z_{ref}}{P_{ref} T_n z_n}$$

The mole fractions $f_{n_x}$ may be measured by the Raman spectrograph 32 of the logging tool 12, which obtains a signal proportional to the number density of each component at each of the zone 24. In the equation above, the pressure $P_n$ at each of the zone-associated depths may be normalized by a factor $P_n/P_{ref}$ to account for wellbore pressure changes between zones 24 that might appear as changes in flow rate, due to the corresponding volumetric changes. Changes in temperature and a compression factor resulting from departures from the ideal gas law may be accounted for by factors $T_{ref}/T_n$ and $z_{ref}/z_n$, where the reference conditions are standard conditions. It follows, then, that the zonal contribution to the $n_{th}$ zone 24 of the $x_{th}$ compositional component may be given by $q_{n_x} = Q_{n_x} - Q_{n-1_x}$.

Most optical measurements provide a response that is proportional to the number density, n, of analyte. For gases this scales with both pressure and temperature (e.g. for ideal gases $n = P/\{k_b T\}$) and, thus, depends on both the well conditions and the fluid composition. To convert this to mole fractions, knowledge of the total density of all molecules in the sample volume 34 is needed. In typical measurements, to calculate mole fractions, an assumption is made that only the analytes capable of being measured optically are present, leading to errors due to the unobserved fraction. In contrast, the techniques described below enable inference of the concentration of unobserved species. Additionally, in order to convert the measured optical response into an absolute number density, an overall system calibration factor may be needed to remove the effect of optical losses throughout the signal path.

This may be done by measuring a reference fluid at the surface prior to a job, but for many measurements this factor may change over time due to optical misalignment or contamination of the windows 36 of the optical module 30, for example. In many configurations, it is relatively difficult to account for this factor in real time and, thus, it increases the error of a measurement. While the techniques described herein attempt to account for variations of this gain and, thus, mitigate the error, it is also possible to implement solutions to prevent window contamination along with the following techniques. As an example, in certain embodiments, a hydrophobic, oleophobic, and/or omniphobic membranes (e.g., such as made out of polytetrafluoroethylene (PTFE)/Teflon) may be utilized to separate the measurement volume within the optical module 30 from the wellbore 14. In such embodiments, water and larger hydrocarbon contaminants may be blocked from entering the measurement volume within the optical module 30, but the gases of interest may diffuse across the barrier and, thus, be measured.

In the disclosed techniques, the temperature and pressure provide an additional constraint on the optical responses proportional to absolute densities, allowing inference of the mole fractions of the sample gas along with either additional components unresolved by the optical measurement or the overall system gain factors. The basic method is to develop the forward model of the tool response as a function of absolute densities of the measured analytes. To provide these inputs, an equation of state is used to predict the absolute densities as a function of pressure, temperature, and mole fractions of the sample gas 34. By adjusting the inputs so that the predicted optical response matches the measured responses, the best fit mole fractions may be inferred by any suitable optimization method (e.g., nonlinear fitting, Bayesian inference, and so forth).

To demonstrate these techniques, a model comprised of Raman scattered signals for l gases and o measurement channels may be considered, $X_i$ that are linearly proportional to the absolute densities of the analytes, $n_j$, through a response matrix, M of size o rows by l columns. As such:

$$\vec{X} = M\vec{n}$$

Similarly, it may be assumed that the ideal gas law holds for all the analytes so that:

$$\vec{n} = \vec{f}\frac{P}{k_b T}$$

where $f_j$ is the mole fraction for analyte, j. Combining these equations and also adding the relationship that the sum of the mole fractions must equal 1:

$$\vec{X} = M\vec{f}\frac{P}{k_b T}$$

$$\sum \vec{f} = 1$$

The system is, thus, over-determined, and it is possible to infer one more parameters of interest. This can be either the overall system calibration factor, G, such that:

$$\vec{X} = G(M\vec{n})$$

or it can be an additional gas that has relatively small overlapping optical responses to the logging tool 12. In this case, the response matrix may be enlarged by one column to include the responses of the unresolved measurements (M of size o rows by l+1 columns). In either case, for a well-defined response matrix, M, enough independent measurements are available to determine all the components of $\vec{f}$.

However, in a real-world system, the response function is likely not to be a simple linear matrix. For example, in a Raman measurement, there could be additional linear response terms due to the densities of the gas (due to index variations with density that effect the sample volume) and an exponential dependence between channels due to absorption such that the signal for a single channel is approximately:

$$X_i = (M_{ij}n_j)(1+3n_k r_k)(10^{-\alpha_{io}n_o l})$$

where $r_k$ is the molar refractivity of gas k, $\alpha_{io}$ is the absorption coefficient of gas o at measurement channel i, and l is the optical path-length within the sample volume. For other measurements, such as transmission optical spectroscopy, the response function may be given by Beer's law:

$$X_i = (10^{-\alpha_{io}n_o l})$$

In many of these nonlinear cases, a preferred embodiment may be to use Bayesian inference as it allows to cleanly define prior knowledge in the region of allowed mole fractions and, thus, ensure the inversion occurs in a unique region. In addition, the embodiments described herein are not limited only to optical measurements, but any measurement whose response is related to the absolute number density of a gas may be used (see, e.g., FIG. 6). Additionally, for many applications, utilizing the ideal gas law may not be accurate enough. Instead, in certain embodiments, an equation of state (EOS) that accounts for interactions between molecules (e.g., a wide range natural gas EOS, the Refprop EOS, and so forth) may be used.

Figure 6:
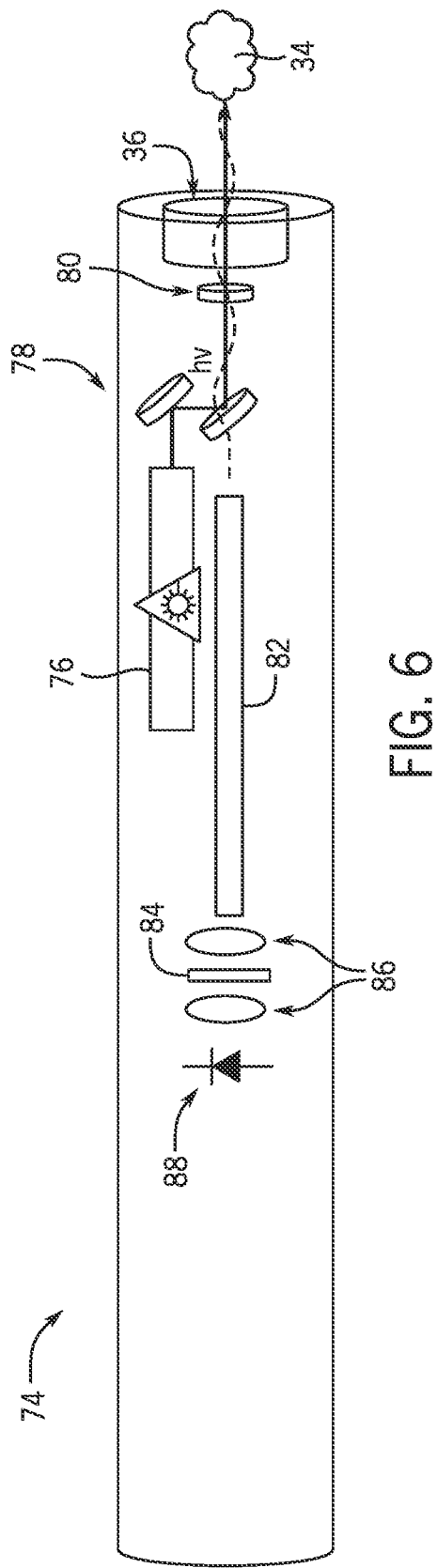
FIG. 6 illustrates another apparatus for detecting hydrogen (or other gases) in a wellbore, in accordance with embodiments of the present disclosure.

FIG. 6 illustrates another apparatus for detecting hydrogen (or other gases) in a wellbore 14. In particular, a logging tool 74 may include a laser 76 and beam steering optics 78 and, in certain embodiments, focusing and collection optics (not shown). In certain embodiments, a reference 80 may be mounted internally. In certain embodiments, Raman scattered photons from a sample 34 may be collected into a fiber 82. In certain embodiments, a bandpass filter 84 may select a specific molecule. In addition, in certain embodiments, lenses 86 may collimate and focus the photons at a photodiode 88. In certain embodiments, the logging tool 74 may be in communication with a data processing system 46 configured to perform the operations described in greater detail herein.

As described above, in certain embodiments, a processing system of the logging tool 12 or another downhole tool may be used to perform the operations of the data processing system 46 described herein. In other words, as opposed to being located at the surface 26, the data processing system 46 described herein may be contained within the logging tool 12 or another downhole tool. In other embodiments, a processing system comprised of two processors, with one in the logging tool 12 or another downhole tool and one at the surface 26 may be configured to perform the operations described herein in conjunction with each other.

The specific embodiments described above have been illustrated by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

In the claims, means-plus-function clauses are intended to cover the structures described herein as performing the recited function and not only structural equivalents, but also equivalent structures. Thus, for example, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words "means for" together with an associated function.

The invention claimed is:

1. A data processing system, comprising:
   one or more processors configured to execute instructions stored on one or more memory media, wherein the instructions, when executed by the one or more processors, cause the data processing system to monitor storage of gas in a well by:
   (a) estimating initial mole fractions of one or more components of the gas being stored in the well based on one or more tool parameters of a logging tool disposed within a wellbore of the well in a zone of a subterranean formation;
   (b) calculating component densities of the one or more components of the gas based at least in part on the initial mole fractions of the one or more components of the gas;
   (c) predicting an optical response and pressure using the one or more tool parameters of the logging tool and the component densities of the one or more components of the gas; and
   (d) comparing the predicted optical response and pressure to an optical response and pressure measured by an optical module of the logging tool to determine whether the estimated initial mole fractions and the calculated component densities of the one or more components of the gas are representative of actual mole fractions and component densities of the one or more components of the gas.

2. The data processing system of claim 1, wherein the gas comprises hydrogen ($H_2$), carbon dioxide ($CO_2$), carbon monoxide (CO), methane ($CH_4$), ethane ($C_2H_6$), propane ($C_3H_8$), butane ($C_4H_{10}$), pentane ($C_5H_{12}$), hexane ($C_6H_{14}$), heptane ($C_7H_{16}$), octane ($C_8H_{18}$), nonane ($C_9H_{20}$), decane ($C_{10}H_{22}$), hydrogen sulfide ($H_2S$), nitrogen ($N_2$), or some combination thereof.

3. The data processing system of claim 1, wherein the instructions, when executed by the one or more processors, cause the data processing system to repeat steps (a)-(d) for the zone if the predicted optical response and pressure do not match the measured optical response and pressure within respective predetermined thresholds.

4. The data processing system of claim 1, wherein the instructions, when executed by the one or more processors, cause the data processing system to move the logging tool to another zone of the subterranean formation, and repeat steps (a)-(d) for the another zone if the predicted optical response and pressure matches the measured optical response and pressure within respective predetermined thresholds.

5. The data processing system of claim 1, wherein the instructions, when executed by the one or more processors, cause the data processing system to monitor the storage of the gas in the well by:
receiving Raman spectrometer signals obtained by the optical module of the logging tool; and
comparing intensity ratios of the Raman spectrometer signals to reference intensity ratios of one or more reference gases to estimate the initial mole fractions of the one or more components of the gas.

6. The data processing system of claim 1, wherein the instructions, when executed by the one or more processors, cause the data processing system to perform an intervention in response to determining that the actual mole fractions and/or the actual component densities of the one or more components of the gas are outside of respective predetermined ranges.

7. The data processing system of claim 1, wherein the one or more tool parameters of the logging tool comprise temperature, pressure, fluid flow rate, measured refraction index, Raman spectrometer signals, or some combination thereof.

8. The data processing system of claim 1, wherein (b) calculating the component densities of the one or more components of the gas comprises calculating the component densities of the one or more components of the gas based at least in part on the initial mole fractions of the one or more components of the gas.

9. The data processing system of claim 1, wherein (c) predicting an optical response and pressure comprises predicting the optical response and pressure using the one or more tool parameters of the logging tool and the component densities of the one or more components of the gas in a forward model.

10. A method for monitoring storage of gas in a well, comprising:
(a) estimating, via a data processing system, initial mole fractions of one or more components of the gas being stored in the well based on one or more tool parameters of a logging tool disposed within a wellbore of the well in a zone of a subterranean formation;
(b) calculating, via the data processing system, component densities of the one or more components of the gas based at least in part on the initial mole fractions of the one or more components of the gas;
(c) predicting, via the data processing system, an optical response and pressure using the one or more tool parameters of the logging tool and the component densities of the one or more components of the gas; and
(d) comparing, via the data processing system, the predicted optical response and pressure to an optical response and pressure measured by an optical module of the logging tool to determine whether the estimated initial mole fractions and the calculated component densities of the one or more components of the gas are representative of actual mole fractions and component densities of the one or more components of the gas.

11. The method of claim 10, wherein the gas comprises hydrogen ($H_2$), carbon dioxide ($CO_2$), carbon monoxide (CO), methane ($CH_4$), ethane ($C_2H_6$), propane ($C_3H_8$), butane ($C_4H_{10}$), pentane ($C_5H_{12}$), hexane ($C_6H_{14}$), heptane ($C_7H_{16}$), octane ($C_8H_{18}$), nonane ($C_9H_{20}$), decane ($C_{10}H_{22}$), hydrogen sulfide ($H_2S$), nitrogen ($N_2$), or some combination thereof.

12. The method of claim 10, comprising repeating steps (a)-(d) for the zone if the predicted optical response and pressure do not match the measured optical response and pressure within respective predetermined thresholds.

13. The method of claim 10, comprising moving the logging tool to another zone of the subterranean formation, and repeating steps (a)-(d) for the another zone if the predicted optical response and pressure matches the measured optical response and pressure within respective predetermined thresholds.

14. The method of claim 10, comprising:
obtaining, via the optical module of the logging tool, Raman spectrometer signals; and
comparing, via the data processing system, intensity ratios of the Raman spectrometer signals to reference intensity ratios of one or more reference gases to estimate the initial mole fractions of the one or more components of the gas.

15. The method of claim 10, comprising performing, via the data processing system, performing an intervention in response to determining that the actual mole fractions and/or the actual component densities of the one or more components of the gas are outside of respective predetermined ranges.

16. The method of claim 10, wherein the one or more tool parameters of the logging tool comprise temperature, pressure, fluid flow rate, measured refraction index, Raman spectrometer signals, or some combination thereof.

17. The method of claim 10, comprising:
(b) calculating, via the data processing system, the component densities of the one or more components of the gas based at least in part on the initial mole fractions of the one or more components of the gas.

18. The method of claim 10, comprising:
(c) predicting, via the data processing system, the optical response and pressure using the one or more tool parameters of the logging tool and the component densities of the one or more components of the gas in a forward model.

19. A logging tool, comprising:
an optical module; and
a data processing system configured to monitor storage of gas in a well by:
estimating initial mole fractions of one or more components of the gas being stored in the well based on one or more tool parameters of the logging tool;

calculating component densities of the one or more components of the gas based at least in part on the initial mole fractions of the one or more components of the gas;

predicting an optical response and pressure using the one or more tool parameters of the logging tool and the component densities of the one or more components of the gas; and comparing the predicted optical response and pressure to an optical response and pressure measured by the optical module to determine whether the estimated initial mole fractions and the calculated component densities of the one or more components of the gas are representative of actual mole fractions and component densities of the one or more components of the gas.

20. The logging tool of claim 19, wherein the gas comprises hydrogen ($H_2$), carbon dioxide ($CO_2$), carbon monoxide (CO), methane ($CH_4$), ethane ($C_2H_6$), propane ($C_3H_8$), butane ($C_4H_{10}$), pentane ($C_5H_{12}$), hexane ($C_6H_{14}$), heptane ($C_7H_{16}$), octane ($C_8H_{18}$), nonane ($C_9H_{20}$), decane ($C_{10}H_{22}$), hydrogen sulfide ($H_2S$), nitrogen ($N_2$), or some combination thereof.

* * * * *